US009145300B1

(12) United States Patent
Foody

(10) Patent No.: US 9,145,300 B1
(45) Date of Patent: Sep. 29, 2015

(54) INTEGRATED HYDROGEN PRODUCTION PROCESS

(71) Applicant: IOGEN CORPORATION, Ottawa (CA)

(72) Inventor: Patrick J Foody, Ottawa (CA)

(73) Assignee: Iogen Corporation, Ontario (CA)

(*) Notice: Subject to any disclaimer, the term of this patent is extended or adjusted under 35 U.S.C. 154(b) by 0 days.

(21) Appl. No.: 14/600,241

(22) Filed: Jan. 20, 2015

(51) Int. Cl.
  *C12P 7/02* (2006.01)
  *C01B 3/48* (2006.01)
  *C12P 3/00* (2006.01)
  *C12P 7/06* (2006.01)

(52) U.S. Cl.
  CPC ... *C01B 3/48* (2013.01); *C12P 3/00* (2013.01); *C12P 7/065* (2013.01); *C01B 2203/0233* (2013.01); *C01B 2203/0283* (2013.01); *C01B 2203/06* (2013.01); *C01B 2203/0827* (2013.01); *C01B 2203/142* (2013.01)

(58) Field of Classification Search
  None
  See application file for complete search history.

(56) References Cited

U.S. PATENT DOCUMENTS

| 4,289,625 | A | * | 9/1981 | Tarman et al. | 210/603 |
|---|---|---|---|---|---|
| 6,136,577 | A | | 10/2000 | Gaddy | |
| 6,340,581 | B1 | | 1/2002 | Gaddy | |
| 8,178,330 | B2 | | 5/2012 | Trevethick et al. | |
| 8,376,736 | B2 | | 2/2013 | Simpson et al. | |
| 8,383,376 | B2 | | 2/2013 | Simpson et al. | |
| 8,507,228 | B2 | | 8/2013 | Simpson et al. | |
| 8,759,047 | B2 | | 6/2014 | Datta et al. | |
| 2007/0049648 | A1 | * | 3/2007 | Shessel | 518/702 |
| 2010/0105118 | A1 | * | 4/2010 | Bell | 435/155 |
| 2010/0317074 | A1 | | 12/2010 | Simpson et al. | |
| 2010/0317077 | A1 | | 12/2010 | Gaddy et al. | |
| 2010/0323417 | A1 | | 12/2010 | Simpson et al. | |
| 2012/0052541 | A1 | | 3/2012 | Oakley | |
| 2012/0156739 | A1 | | 6/2012 | Schultz | |
| 2013/0203142 | A1 | | 8/2013 | Young | |
| 2013/0210096 | A1 | | 8/2013 | Schultz et al. | |
| 2013/0252299 | A1 | | 9/2013 | Bell et al. | |
| 2013/0266997 | A1 | | 10/2013 | Hickey et al. | |
| 2014/0227752 | A1 | | 8/2014 | Datta et al. | |

FOREIGN PATENT DOCUMENTS

| WO | WO 00/68407 A1 | 11/2000 | |
|---|---|---|---|
| WO | WO 02/08438 * | 1/2001 | C12P 7/06 |
| WO | WO 2009/058028 A1 | 5/2009 | |
| WO | WO 2012/062631 A1 | 5/2012 | |
| WO | WO 2012/087949 A2 | 6/2012 | |
| WO | WO 2013/036147 A2 | 3/2013 | |
| WO | WO 2013/119866 A1 | 8/2013 | |
| WO | WO 2014/077705 A1 | 5/2014 | |

OTHER PUBLICATIONS

Ronald Colwell "Oil Refinery Processes a Brief Overview" Copyright © 2009 Process Engineering Associates, LLC, 36 pages.*
Costa et al. "Ethanol to Gasoline Process: Effect of Variables, Mechanism, and Kinetics" Ind. Eng. Chem. Process Des. Dev. 1985, 24, 239-244.*
Dernotte et al. "Evoluotion of Butonol-Gosoline Blends in o Port Fuel-iniection, Spork-Ignition Engine".*
Tarun et al. "Techno-economic study of CO2 capture from natural gas based hydrogen plants" International J. of Greenhouse Gas Control 1 (2007) 55-61.*
Dernotte et al. "Evaluation of Butanol—Gasoline Blends in a Port Fuel-injection, Spark-Ignition Engine" Oil & Gas Science and Technology—Rev. IFP, vol. 65 (2010), No. 2, pp. 345-351.*
Bonaquist, "Analysis of $CO_2$ Emissions, Reductions, and Capture for Large-Scale Hydrogen Production Plants," Praxair White Paper, Oct. 2010.
Chen et al., "An experimental study on carbon monoxide conversion and hydrogen generation from water gas shift reaction," Energy Conversion and Management 49 (2008) 2801-2808.
Collodi et al., "Hydrogen Production via Steam Reforming with $CO_2$ Capture," Chemical Engineering Transactions, vol. 19, 2010, pp. 37-42.
Contadini et al., "Hydrogen production plants: emissions and thermal efficiency analysis," Presented at the Second International Symposium on Technological Environmental Topics in Transports, Oct. 2000, Milan Italy.
Datar et al., "Fermentation of Biomass-Generated Producer Gas to Ethanol," Biotechnology and Bioengineering, Vo. 86, No. 5, Jun. 5, 2004, pp. 587-594.
Najafpour et al., "Ethanol and acetate synthesis from waste gas using batch culture of *Clostridium ljungdahlii*," Enzyme and Microbial Technology 38 (2006) 223-228.
Phillips et al., "Synthesis Gas as Substrate for the Biological Production of Fuels and Chemicals," Applied Biochemistry and Biotechnology, vol. 45/46, 1994 pp. 145-157.
Spath et al., "Life Cycle Assessment of Hydrogen Production via Natural Gas Steam Reforming," National Renewable Energy Laboratory NREL/TP-570-27637, Feb. 2001.
Worden et al., "Production of Butanol and Ethanol from Synthesis Gas via Fermentation." presented at "Biotechnology for the Production of Clean Fuels", Aug. 27-28, 1990, Washington, USA.

* cited by examiner

*Primary Examiner* — Thane Underdahl
(74) *Attorney, Agent, or Firm* — Knobbe Martens Olson & Bear LLP

(57) ABSTRACT

The present invention provides an integrated process for producing a fermentation product from fossil carbon and hydrogen present in a purge gas stream resulting from a hydrogen production process. According to the invention, a purge gas stream obtained from a hydrogen production process is fermented with microorganisms in one or more bioreactors to produce the fermentation product. A fermentation exhaust gas stream from the one or more bioreactors comprising hydrogen, carbon monoxide and/or methane is then obtained and heat is generated therefrom to provide energy for a reforming unit that forms part of the hydrogen production process.

20 Claims, 2 Drawing Sheets

INTEGRATED HYDROGEN PRODUCTION PROCESS

TECHNICAL FIELD

The present invention provides a process for producing a fermentation product from fossil carbon and hydrogen resulting from hydrogen production.

BACKGROUND

Hydrogen is currently used in large quantities in the chemical and petroleum industries. In the chemical industry, hydrogen is mainly used to make ammonia for soil fertilizer via the Haber process involving the reaction of nitrogen gas and hydrogen to produce the ammonia. Hydrogen is also used in oil refineries to upgrade petroleum-based compounds in hydroprocessing unit operations that require hydrogen, such as hydrocracking and hydrotreating processes. These processes often aid in lowering the sulfur content of the finished fuel product. The use of hydrogen in refineries is expected to increase due to an increased demand for low sulfur fuels driven by environmental concerns.

The literature describes a variety of different processes to make hydrogen, many of which are the subject of significant research and development efforts. Some of the processes disclosed include biomass pyrolysis or gasification and biological processes, such as bacterial fermentation and enzymatic hydrogen production. Electrolysis is another technology for making hydrogen in which water is decomposed into oxygen and hydrogen. Currently, however, hydrogen is produced commercially from fossil methane. Such production processes are inexpensive and the natural gas feedstock for the process is widely available and relatively low cost.

The production of hydrogen from methane includes a reforming reaction in which the methane is converted to carbon monoxide and hydrogen. A commonly utilized reforming reaction is steam methane reforming (SMR) that converts the methane into hydrogen and carbon monoxide in the presence of steam. Among other known reforming reactions is autothermal reforming, which uses oxygen and carbon dioxide or oxygen and steam in a reaction with methane to form carbon monoxide and hydrogen. Reforming is followed by one or more water gas shift (WGS) reactions in a reactor in which the carbon monoxide and hydrogen are converted to carbon dioxide and additional hydrogen. Hydrogen is then recovered from an outlet stream of the WGS reactor. An example of such a recovery technique is pressure swing adsorption (PSA), which is used to separate gas species from a mixture of gases under pressure using adsorbent materials such as zeolites, molecular sieves or activated carbon. The adsorbent material absorbs the target gas species at high pressure and the separation relies on the different affinity of various gas species in the gas stream. As the pressure is lowered, the target gas desorbs. When used to recover hydrogen, pressure swing adsorption adsorbs hydrogen and the desorption results in a stream concentrated in hydrogen. A stream comprising non-adsorbed species is also generated by pressure swing adsorption, which is often referred to as a purge gas stream.

In existing commercial operations, the purge gas stream is burned to provide process heat. Such heat integration is advantageous as many of the unit operations in hydrogen production operate at high temperature. In a typical hydrogen production process, the purge stream is fed to an SMR furnace that provides heat energy for the methane reforming reaction.

The composition of the purge gas stream varies depending on the operating parameters in the upstream reforming. Components present in this stream may include hydrogen and additionally carbon dioxide, carbon monoxide and/or methane. Hydrogen is present since its recovery in the pressure swing adsorption or other hydrogen recovery operation is incomplete.

Despite the advantages of heat integration, the presence of hydrogen in purge streams is a significant drawback. Hydrogen is costly and simply burning it for heat production is an inefficient use of this component. This in turn reduces the economics of the process. Accordingly, there is a need in the art to better utilize constituents of the purge gas, particularly hydrogen, without significantly disrupting the operation of the hydrogen production process.

SUMMARY

Embodiments of the present invention provide a process for producing a fermentation product from a stream comprising fossil hydrogen resulting from hydrogen production. Processes disclosed herein include producing a fermentation product from a purge stream resulting from a hydrogen production process and for integrating such stream into the hydrogen production process.

Embodiments of the invention relate to a process in which the energy value of the components in a purge stream, particularly hydrogen resulting from hydrogen production, is converted to a fermentation product, thereby maximizing the product output of hydrogen plants. According to aspects of the process described further herein, a purge stream from hydrogen production is fermented in one or more bioreactors by microorganisms to produce the fermentation product, including products such as a fuel, fuel intermediate or chemical product. In addition, process energy in the form of heat is provided to a reforming unit of a hydrogen production process by a fermentation exhaust gas stream obtained from one or more bioreactors in which the fermentation is conducted. Thus, a valuable fermentation product is produced from hydrogen that is present in a purge gas stream which would otherwise be burned for process energy, with the added benefit of enabling heat integration within the hydrogen production process.

Furthermore, because hydrogen is converted to a fermentation product during the fermentation reaction, there is less hydrogen in the purge stream remaining to combust in order to generate heat for the reforming. Thus, according to embodiments of the invention, to compensate for this loss, the hydrogen utilized in the fermentation is replaced with a fuel gas, such as fossil methane, which is used to generate heat for reforming. This involves adding the fuel gas to the fermentation exhaust stream and/or to a reforming unit. In various embodiments the amount of fuel gas used to provide such heat is at least the heat of combustion of the fermentation product produced in the fermentation.

When methane is utilized as a fuel gas, this is particularly advantageous since hydrogen is significantly more costly than methane. Thus, by fermenting hydrogen and subsequently replacing at least a portion of the energy of the hydrogen consumed with fossil methane, a higher value component that is converted to a fermentation product is replaced by low cost fossil methane.

A further advantageous feature of certain embodiments of the invention is an increased efficiency in production of the fermentation product by the microorganism since the purge stream contains reduced amounts of carbon monoxide due to the water-gas shift which converts syngas to carbon dioxide and hydrogen. As carbon monoxide can have toxic effects on bacteria or other microorganisms used to produce the fermentation product, by fermenting a purge gas stream having reduced carbon monoxide content, the fermentation can potentially proceed with reduced inhibition, which in turn may increase the efficiency of the process.

Furthermore, in certain embodiments of the invention in which the fermentation product is a fuel such as an alcohol, and hydrogen production is carried out to upgrade petroleum-based compounds in a refinery, the fuel fermentation product can be readily used as a constituent in a refined product either directly or after subsequent processing. An example of such subsequent processing is described herein. Thus, embodiments of the present invention can enable the production of additional product produced from a waste stream for addition to a refined product produced in an oil refinery, thereby increasing product output from the refinery from a waste stream that would otherwise be burned.

According to one aspect of the invention, there is provided an integrated hydrogen production process comprising (i) providing a purge gas stream obtained from a process comprising the steps of: (a) converting fossil methane to carbon monoxide and hydrogen by reforming in a reforming unit, (b) converting at least a portion of the carbon monoxide by a water-gas shift reaction to carbon dioxide, thereby producing a stream comprising carbon dioxide and hydrogen, and (c) separating at least a portion of the hydrogen from the stream of step (b) from non-hydrogen components to produce a stream enriched in hydrogen and a purge gas stream comprising hydrogen and at least one of carbon dioxide, methane and carbon monoxide; (ii) fermenting the purge gas stream, or a portion thereof, with microorganisms in one or more bioreactors to produce the fermentation product; (iii) providing a fermentation exhaust gas stream from the one or more bioreactors, the exhaust gas stream comprising one or more combustible gases; (iv) generating heat from the exhaust gas stream and using the heat to provide energy for the reforming unit; and (v) generating additional heat from a fuel gas stream and using the heat produced from the fuel gas stream to provide energy for the reforming unit, wherein the rate of fuel gas used to provide such additional heat is at least the rate of production of product energy associated with the fermentation product produced in step (ii).

According to a further aspect of the invention, there is provided an integrated hydrogen production process comprising: (i) providing a purge gas stream obtained from a hydrogen production process comprising the steps of: (a) converting fossil methane to carbon monoxide and hydrogen by reforming in a reforming unit, (b) converting at least a portion of the carbon monoxide by a water-gas shift reaction to carbon dioxide, thereby producing a stream comprising carbon dioxide and hydrogen, and (c) separating at least a portion of the hydrogen from the stream of step (b) from non-hydrogen components to produce a stream enriched in hydrogen and a purge gas stream comprising hydrogen and at least one of carbon dioxide, methane and carbon dioxide; and (ii) fermenting the purge gas stream, or a portion thereof, in one or more bioreactors with a bacterial strain from the genus *Clostridium* to produce ethanol; (iii) providing a fermentation exhaust gas stream from the one or more bioreactors, the exhaust gas stream comprising one or more combustible gases; and (iv) generating heat from the exhaust gas stream and using the heat to provide energy for the reforming unit.

According to a further aspect of the invention, there is provided an integrated hydrogen production process comprising: (i) providing a purge gas stream obtained from a process comprising the steps of: (a) converting fossil methane to carbon monoxide and hydrogen by reforming in a reforming unit, (b) converting at least a portion of the carbon monoxide by a water-gas shift reaction to carbon dioxide, thereby producing a stream comprising carbon dioxide and hydrogen, and (c) separating at least a portion of the hydrogen from the stream of step (b) from non-hydrogen components to produce a stream enriched in hydrogen and a purge gas stream comprising hydrogen and at least one of carbon dioxide, methane and carbon monoxide; (ii) fermenting the purge gas stream, or a portion thereof, with microorganisms in one or more bioreactors to produce an alcohol; (iii) providing a fermentation exhaust gas stream from the one or more bioreactors, the exhaust gas stream comprising one or more combustible gases; (iv) generating heat from the exhaust gas stream and using the heat to provide energy for the reforming unit; and (v) providing the hydrogen produced in step (i)(c) to a hydroprocessing unit in an oil refinery and using the alcohol produced in step (ii) as a constituent in a refined product either directly or after subsequent processing.

In another aspect of the invention, there is provided an integrated hydrogen production process comprising: (i) providing a purge gas stream obtained from a process comprising the steps of: (a) converting fossil methane to carbon monoxide and hydrogen by reforming in a reforming unit, (b) converting at least a portion of the carbon monoxide by a water-gas shift reaction to carbon dioxide, thereby producing a stream comprising carbon dioxide and hydrogen, and (c) separating at least a portion of the hydrogen from the stream of step (b) from non-hydrogen components to produce a stream enriched in hydrogen and a purge gas stream comprising hydrogen and at least one of carbon dioxide, methane and carbon monoxide; (ii) fermenting the purge gas stream, or a portion thereof, with microorganisms in one or more bioreactors to produce a fermentation product that is an alcohol, an organic acid or a salt of an organic acid; (iii) providing a fermentation exhaust gas stream from the one or more bioreactors, the exhaust gas stream comprising one or more combustible gases; and (iv) generating heat from the exhaust gas stream and using the heat to provide energy for the reforming unit.

DETAILED DESCRIPTION

Hydrogen Production Process

Figure 1:
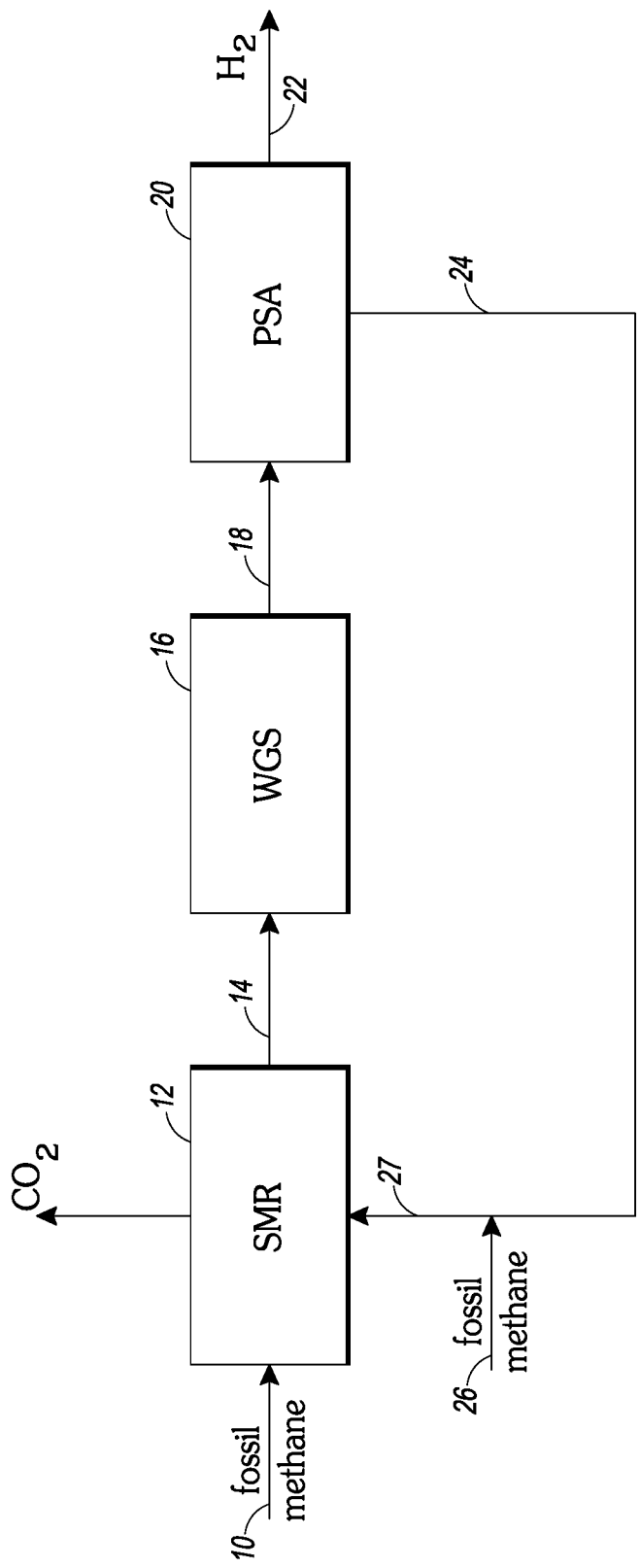
FIG. 1 is a flow diagram depicting a comparative process describing an integrated hydrogen production process in which fermentation of a purge gas stream from hydrogen production is not conducted.

The feedstock for the hydrogen production process is fossil methane. The fossil methane will typically be withdrawn from a natural gas pipeline. As would be appreciated by those of skill in the art, before natural gas is introduced to a pipeline it is generally processed to remove impurities and compressed.

The fossil methane withdrawn from the pipeline, or obtained from other sources, is fed to a reforming step that is part of a hydrogen production process. During reforming, the fossil methane is converted to carbon monoxide and hydrogen in a reforming unit. Examples of reforming reactions that can be utilized in the practice of the invention include steam methane reforming (SMR), autothermal reforming (ATR), partial oxidation and dry reforming.

Both steam methane reforming and authothermal reforming methods operate by exposing methane, usually in the presence of a catalyst, to high temperature and pressure to produce syngas, which is a mixture comprising hydrogen and carbon monoxide. Steam methane reforming is often referred to as a non-oxidative process that converts the methane into hydrogen and carbon monoxide in the presence of steam by the following reaction:

$$CH_4+H_2O \rightarrow CO+3H_2$$

Autothermal reforming uses oxygen and carbon dioxide or oxygen and steam in a reaction with methane to form carbon monoxide and hydrogen. The authothermal reaction using oxygen and carbon dioxide can be described by the following reaction:

$$2CH_4+O_2+CO_2 \rightarrow 3H_2+3CO+H_2O$$

The autothermal reaction using oxygen and steam proceeds by the following reaction:

$$4CH_4+O_2+2H_2O \rightarrow 10H_2+4CO$$

Partial oxidation involves the addition of oxygen and may proceed via the following equation:

$$CH_4+1/2O_2 \rightarrow CO+2H_2$$

Dry reforming processes involve converting the fossil methane and carbon dioxide in the absence of water addition to hydrogen, carbon monoxide and water.

In one embodiment of the invention, fossil methane is fed to reformer tubes in a reforming unit. The reforming reaction to produce carbon monoxide and hydrogen is conducted in these tubes and typically contains a catalyst, which catalyzes the reforming reaction to produce carbon monoxide and hydrogen. The reformer tubes are heated by the combustion of fossil methane or other fuel gas.

Reforming is followed by a water gas shift reaction to produce carbon dioxide and hydrogen. For example, steam methane reforming followed by a water gas shift converts natural gas to carbon dioxide and hydrogen as follows:

$$CH_4+H_2O \rightarrow CO+3H_2$$

$$CO+H_2O \rightarrow CO_2+H_2$$

Overall: $CH_4+2H_2O \rightarrow CO_2+4H_2$

In one embodiment of the invention, the carbon monoxide content of the stream resulting from the water gas shift may be less than 10 mol %, less than 8 mol % or less than 5 mol % (mol:mol).

In one embodiment of the invention, the water gas shift includes at least a high temperature shift, which is a shift reaction conducted at a temperature of at least 250° C., typically higher than 300° C. Subsequent to a high temperature shift, a low temperature shift is optionally conducted. The low temperature shift occurs at a lower temperature than a high temperature shift, such as a temperature lower than 300° C., more typically less than 250° C. The high temperature shift generally results in the incomplete conversion of carbon monoxide. A low temperature shift may increase such conversion, thereby reducing the carbon monoxide concentration further. This may produce an outlet stream having a carbon monoxide level of less than 5 mol %, less than 3 mol %, more typically less than 2 mol %. Both high and low temperature shifts are generally carried out in the presence of a catalyst.

The hydrogen produced by the water gas shift reaction can be recovered from non-hydrogen components, including carbon dioxide, from a gaseous or liquid stream using known techniques employing adsorbents or membranes. An example of a recovery technique using adsorbents is pressure swing adsorption, which is commonly used to recover hydrogen produced by steam methane reforming. As would be appreciated by those of skill in the art, pressure swing adsorption is used to separate gas species from a mixture of gases under pressure using adsorbent materials such as zeolites, molecular sieves and/or activated carbon. The adsorbent material absorbs the target gas species at high pressure and the separation relies on the different affinity of various gas species in the gas stream. When the pressure is lowered, the target gas desorbs. In the practice of various embodiments of the present invention, pressure swing adsorption adsorbs hydrogen and the desorption results in a stream concentrated in hydrogen. The stream concentrated in hydrogen may contain greater than 90 mol % or 95 mol % hydrogen.

A stream comprising non-adsorbed species, including carbon dioxide, among other components, is also generated by pressure swing adsorption. This latter stream comprising carbon dioxide is referred to as a purge gas stream. The other components in the purge gas stream may include carbon monoxide, methane, hydrogen or a combination of such components.

The purge gas stream is introduced to a bioreactor and fermented to produce a fermentation product as set out below. However, a portion of the purge gas stream can optionally be used to generate heat for the process. For example, a portion of the purge gas stream can be drawn off as a bypass stream and fed to an SMR furnace where it is combusted and the heat generated used to provide energy to the reforming unit with the balance of the stream then being fed to a bioreactor. Such a configuration is described in more detail below.

Fermentation of Purge Gas

The production of a fermentation product from the purge gas may be carried out with acetogenic microorganisms. Examples of fermentation products include alcohols and organic acids. Microorganisms useful in the practice of the invention may include any bacteria from a genus selected from *Acetogenium, Acetobacterium, Acetoanaerobium, Butyribacterium* and *Clostridium* that are capable of converting components in the purge gas to an alcohol, organic acid and/or salt thereof. Examples of suitable salts include sodium and potassium salts of the organic acid, such as sodium acetate and potassium acetate.

In certain embodiments of the invention, the fermentation product is ethanol or butanol. Depending on the constituents in the purge gas, the reactions carried out by a microorganism to produce ethanol may include the following:

$$6CO+3H_2O \rightarrow CH_3CH_2OH+4CO_2$$

$$6H_2+2CO_2 \rightarrow CH_3CH_2OH+3H_2O$$

In a further embodiment of the invention, the microorganism used to produce ethanol is from the genus *Clostridium*. Without being limiting, a particularly suitable microorganism for producing ethanol from the biogenic carbon dioxide and fossil derived hydrogen is *Clostridium ljungdahlii*. This bacterium can effectively convert biogenic carbon dioxide and hydrogen to ethanol.

Figure 2:
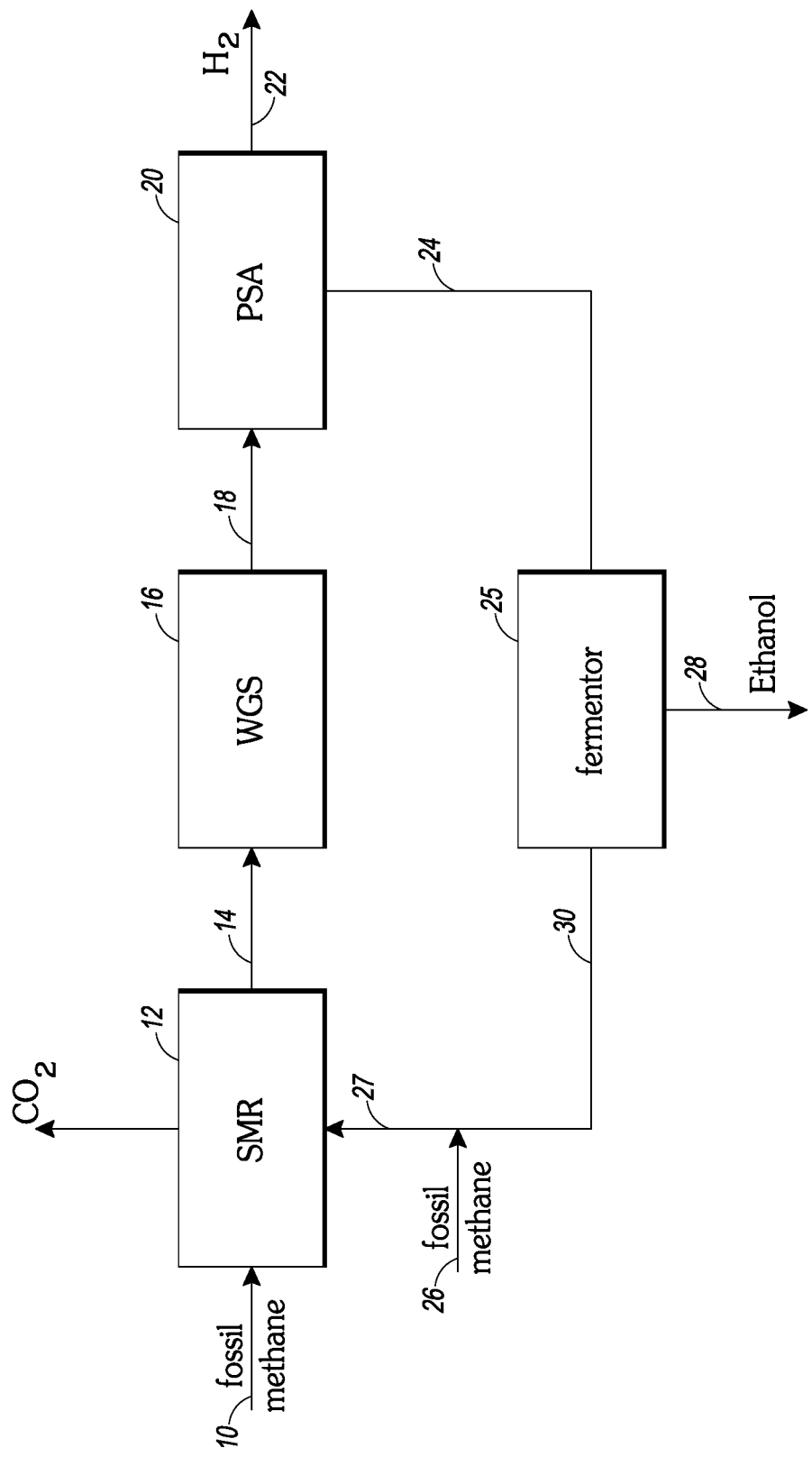
FIG. 2 is a flow diagram depicting an embodiment of the invention in which fermentation of a purge gas stream from hydrogen production is conducted to produce ethanol as part of an integrated hydrogen production process.

A representative example of a process in which the purge gas stream is fermented to produce ethanol is provided in FIG. 2.

While the production of ethanol from carbon dioxide and hydrogen has been described, acetogenic microorganisms can also produce acetic acid from these gaseous substrates. For example, *Clostridium* species are known to produce acetic acid by the following reaction mechanism:

$$4H_2+2CO_2 \rightarrow CH_3COOH+2H_2O$$

As would be appreciated by those of skill in the art, acetic acid, acetate or both of these species will be present in solution as dictated by the pH of the solution. Another potential fermentation product is butyric acid.

The purge gas is fermented to produce the fermentation product in a bioreactor or a plurality of such reactors. The purge gas may be introduced to a bioreactor comprising a liquid nutrient broth comprising the bacteria and components required for their growth, such as vitamins and salts. In one embodiment of the invention, the bioreactor is one of a plurality of bioreactors in a system in which the reactors are arranged in series, parallel or a combination of such arrangements. A growth reactor may also be utilized which feeds a separate bioreactor in which most of the ethanol product is produced or a growth phase can be carried out in a fermentation bioreactor itself.

The bioreactor for conducting the conversion can be a stirred or an unmixed tank reactor. An example of a bioreactor that can be used to ferment the purge gas is a deep tank bioreactor, which is a reactor generally having a depth of greater than 10 meters. The deep tank reactor may be stirred to facilitate contact between the gases and the liquid nutrient broth. The gases may also be introduced at the bottom region of the bioreactor and bubble through the liquid broth. Optionally, the gases are introduced along with the liquid broth, such as together with a broth re-circulation stream. Mechanical pumping may also be utilized to facilitate liquid flow and mass transfer. Another type of reactor that can be utilized in the practice of the invention is a gas lift reactor.

The bioreactor may employ cell recycle in order to replenish the concentration of cells in the reactor. According to such embodiments, a liquid stream comprising cells is withdrawn from the reactor and sent to a solids-liquid separation to separate cells from the stream. The separated cells are returned to the reactor and a cell-free stream resulting from the separation is sent to product recovery to recover the fermentation product, typically by distillation.

Gases may accumulate in the headspace of the reactor. Such gases may be recycled back to the bioreactor. The gases withdrawn from the reactor may be combined with a stream comprising carbon dioxide and hydrogen introduced to the reactor.

Carbon dioxide produced during the hydrogen production process can also be recovered and used in various ways. For example, the carbon dioxide that is recovered can be vented, used to make a product therefrom, used in enhanced oil or gas recovery, vented or blended with another stream and combusted, and/or introduced to the fermentation along with the purge gas stream. Carbon dioxide can be recovered from any carbon dioxide containing-stream produced or derived from the hydrogen production process. An example of a stream from which carbon dioxide can be recovered is a stream exiting a water gas shift unit and upstream of a PSA unit. Moreover, carbon dioxide can be recovered upstream of a water gas shift reaction. An example of such a stream is a flue gas stream exiting the reforming unit. Recovery of carbon dioxide from a carbon dioxide-containing stream can be carried out using known techniques, including processes using adsorbents, membranes, solvents and/or other suitable techniques known to those of skill in the art. Recovery of carbon dioxide upstream of fermentation is advantageous since it can reduce costs associated with compression. For example, if a purge gas stream is compressed prior to fermentation, it is advantageous to remove carbon dioxide prior to such compression to improve the economics of this step.

As mentioned, in certain embodiments of the invention in which the fermentation product is a fuel such as an alcohol, and hydrogen production is carried out to upgrade petroleum-based compounds in a refinery, the fuel fermentation product can be readily used as a constituent in a refined product produced in the refinery either directly or after subsequent processing. Such refined product includes, for example, gasoline, diesel and/or jet fuel. Direct use may include blending the alcohol with the refined product to produce a blend of alcohol and refined product/alcohol, such as a gasoline/ethanol or gasoline/butanol blend. A non-limiting example of subsequent processing of the alcohol includes the use of a zeolite catalyst to convert the alcohol, such as ethanol, into a hydrocarbon, using known technology. The hydrocarbon can subsequently be blended with a refined product such as gasoline, diesel and/or jet fuel.

Fermentation Exhaust Gas Stream

As noted previously, in various embodiments a fermentation exhaust gas stream, which includes any stream comprising combustible components that are gaseous under standard temperature and pressure, is withdrawn from one or more of the bioreactors. The fermentation exhaust gas stream comprises one or more gases that are combustible. The term "combustible" is used in its ordinary sense to refer to a flammable component that is reactive with oxygen. For example, in one embodiment of the invention, the exhaust gas comprises a combustible gas that includes at least one of methane, carbon monoxide and hydrogen. In a further embodiment, the exhaust gas stream comprises at least one of methane and carbon monoxide. It may further comprise other gaseous components such as carbon dioxide and/or other non-combustible gases.

The fermentation exhaust gas stream withdrawn from one or more of the bioreactors is used to generate heat to provide energy for the reforming unit. The heat generation may involve feeding the exhaust gas stream, or a portion thereof, to a furnace where the exhaust gas stream is combusted. In one embodiment of the invention, the exhaust gas stream may be combusted in gas burners that heat reformer tubes in which the reforming reaction occurs. During combustion, the exhaust gas stream may be mixed with ambient air to facilitate combustion. The exhaust gas stream may be combusted in the furnace along with fossil methane or other fuel gases such as naphtha.

A flue gas stream from the reforming unit is typically vented to atmosphere. This stream is produced upon the combustion of the fermentation exhaust stream and optionally the fuel gas used for supplying heat to the reforming stage.

As set out previously, in various embodiments a portion of the purge gas stream rather than the full stream can be used to generate heat for the process. For example, prior to introducing the purge gas stream to a bioreactor, the purge gas stream may be subjected to a gas separation step using membranes or adsorbents to separate carbon dioxide and/or hydrogen from other gaseous components in the purge gas stream. A separated stream comprising the carbon dioxide and/or hydrogen can subsequently be fed to a bioreactor and converted to the fermentation product. A second stream resulting from the separation comprising the other gaseous components, which may include carbon monoxide, methane or a combination thereof, may be introduced to the furnace of a reforming unit to generate heat for use therein, as set out previously.

Fuel Gas Stream

In addition to generating heat from the exhaust gas stream and providing it to the reforming step, heat may be generated from a fuel gas stream. According to such embodiments, the heat from both the exhaust gas stream and a fuel gas stream is used to provide energy for the reforming unit. The fuel gas stream may be added to a reforming unit or fed to the exhaust gas stream to produce a combined stream. The heat can be generated from the separate streams individually or the combined stream. In one embodiment of the invention, the fuel gas is methane, naptha, coal gas, diesel and/or gasoline. In a further embodiment, the fuel gas comprises methane and additionally other combustible gaseous components. Methane may be present in the fuel gas as a predominant or a minor component.

Methane is a fuel gas that is particularly suitable for use in the invention. Such an embodiment is particularly advantageous since hydrogen is significantly more costly than fossil methane. Thus, by fermenting hydrogen and replacing at least a portion of the hydrogen consumed with fossil methane, the process economics can be improved, while maximizing the product output of a hydrogen plant.

The rate of fuel gas used to replace the hydrogen is quantified as a heat of combustion times the flow rate, which is measured in the units of BTU/hr. In various embodiments the rate of fuel gas used for heat generation in the reforming is at least the rate of production of fermentation product energy, which is the heat of combustion of the fermentation product produced by fermentation times the quantity of fermentation product, measured in units of BTU/hr. In one embodiment, the rate of fuel gas used for heat generation is at least 1.15 times the rate of production of fermentation product energy. In a further embodiment, the rate of fuel gas used for heat generation is at least 1.20 times the rate of production of fermentation product energy. In another embodiment, the rate of fuel gas used for heat generation is at least 1.40 times or as much as 2.00 times the rate of production of fermentation product energy. The heat of combustion is a lower heating value (LHV) as determined by Boundy et al., Biomass Energy Data Book (2011), U.S. Department of Energy, Edition 4, Prepared by Oak Ridge National Laboratory, Appendix A, Lower and Higher Heating Values of Gas, Liquid and Solid Fuels, which lists the BTU per volume or weight for various gaseous and liquid fuels (incorporated herein by reference). For fuels not listed in the foregoing reference, the heat of combustion is measured by standard ASTM methodology, using ASTM D240-14 (2014) for liquid fuels or ASTM D4868-00 (2010) for gaseous fuels (each of which are also incorporated herein by reference).

EXAMPLES

This example demonstrates that by fermenting hydrogen, among other components in a purge gas stream, and subsequently replacing at least a portion of the energy of the hydrogen consumed with a fuel gas, in this case fossil methane, the economics of the process can be improved relative to a process conducted without utilizing a fermentation.

In order to illustrate such improvement, a comparative process is first described in which a purge gas stream resulting from hydrogen purification by pressure swing adsorption is fed directly to a reforming step, without implementing a fermentation step. In this comparative process, hydrogen, among other components present in the purge stream, is combusted to provide heat to a steam methane reforming unit. The energy balance for this process was determined and the results are shown in Table 1 below. This is followed by a description of an embodiment of the invention in which the purge stream resulting from the pressure swing adsorption is fermented to produce a fermentation product and a fermentation exhaust stream is fed to the reforming step. Methane is added to the fermentation exhaust at an amount that corresponds at least to the heat of combustion of the fermentation product produced by the fermentation. The energy balance for this latter process is described below in Table 2.

An analysis of the energy balance of the comparative process versus the process conducted according to an embodiment of the invention reveals that by utilizing hydrogen for production of a fermentation product, and replacing the hydrogen by fossil methane, the process economics of the hydrogen production process can be significantly improved. While more fossil methane is used, a higher value hydrogen component of the purge gas is converted to a valuable fermentation product rather than being burned. The increases in revenue from ethanol more than off-set the additional methane use.

The comparative process is described with reference to FIG. 1. As shown in this figure, fossil methane 10 is fed to a steam methane reforming (SMR) unit 12. The outlet from the SMR unit 12 is a syngas stream 14 comprising carbon monoxide, hydrogen, carbon dioxide and methane. The syngas stream 14 from the SMR unit 12 is fed to a water gas shift (WGS) unit 16. The WGS unit 16 produces a water-gas shift outlet stream 18 enriched in hydrogen and additionally comprising carbon dioxide, methane and carbon monoxide. Water-gas shift outlet stream 18 is subsequently fed to a pressure swing adsorption (PSA) unit 20 to produce a hydrogen-enriched stream 22 and a purge gas stream 24 comprising hydrogen, carbon dioxide, methane and carbon monoxide. Fossil methane make-up stream 26 is added to the purge gas stream 24. After addition of fossil methane make-up stream 26, the resultant combined stream 27 is fed to the SMR unit 12 as a process energy source.

The energy balance for the comparative process illustrated in FIG. 1 is described in Table 1 below. For all energy balance calculations set forth below, it is assumed that methane and carbon monoxide do not participate in the fermentation reaction and that there are no losses of hydrogen in the purge stream. Additionally, it is assumed that that yield of hydrogen to ethanol is 92%, that there are no losses of ethanol and that acetic acid is not produced as a byproduct.

TABLE 1

Energy balances for the comparative process

| Stream name | Stream No. (FIG. 1) | Energy (MMBTU/hr) |
| --- | --- | --- |
| Fossil methane | 10 | 1400 |
| Syngas | 14 | 1635 |
| Water-gas shift outlet | 18 | 1614 |
| Hydrogen-enriched stream | 22 | 1168 |
| Purge gas | 24 | 446 |
| Fossil methane make-up | 26 | 152 |
| Total fuel to SMR | 27 | 598 |

An embodiment of the inventive process is described with reference to FIG. 2. Like references numbers among FIG. 1 and FIG. 2 depict similar or identical unit operations or process streams. As shown in FIG. 2, fossil methane 10 is fed to a steam methane reforming (SMR) unit 12. The outlet from the SMR unit 12 is a syngas stream 14 comprising carbon monoxide, hydrogen, carbon dioxide and methane. The syngas stream 14 from the SMR unit 12 is fed to a water gas shift (WGS) unit 16. The WGS unit 16 produces a stream 18 enriched in hydrogen and additionally comprising carbon dioxide, methane and carbon monoxide. Stream 18 is subsequently fed to a pressure swing adsorption (PSA) unit 20 to produce a stream enriched in hydrogen 22 and a purge gas stream 24 comprising hydrogen, carbon dioxide, methane and carbon monoxide.

Unlike the comparative process of FIG. 1, in the process of FIG. 2, the purge gas stream 24 comprising hydrogen, carbon dioxide, methane and carbon monoxide is fed to a fermentor 25. In the fermentor 25 a *Clostridium ljungdahlii* bacteria ferments the hydrogen, carbon dioxide and carbon monoxide to ethanol via the following reactions:

$$6CO + 3H_2O \rightarrow CH_3CH_2OH + 4CO_2$$

$$6H_2 + 2CO_2 \rightarrow CH_3CH_2OH + 3H_2O$$

A fermentation broth comprising ethanol is withdrawn from the fermentor 25 as ethanol stream 28 and then concentrated by distillation. A gaseous exhaust stream 30 is withdrawn from the headspace of the fermentor 25 and a fossil methane stream 26 is added to the fermentation exhaust stream 30. After addition of the fossil methane stream 26, the resultant combined stream 27 is fed to the SMR unit 12 as a process energy source. The amount of fossil methane added to the exhaust gas stream 30 via the fossil methane stream 26 to provide heat to the SMR unit 12 is sufficient to provide at least the heat of combustion of the fermentation product, in this case ethanol in the ethanol stream 28 produced in the fermentor 25.

The energy balance for the above-described process is provided in Table 2 below.

TABLE 2

Energy balance for the process comprising fermentation of purge gas

| Stream name | Stream No. (FIG. 2) | Energy (MMBTU/hr) |
|---|---|---|
| Fossil methane | 10 | 1400 |
| Syngas | 14 | 1635 |
| Water-gas shift outlet | 18 | 1614 |
| Hydrogen-enriched stream | 22 | 1168 |
| Purge gas | 24 | 446 |
| Gaseous exhaust gas stream | 30 | 301 |
| Fossil methane make-up | 26 | 298 |
| Ethanol stream | 28 | 110 |
| Total fuel to SMR | 27 | 598 |

As discussed, one difference between FIG. 1 and FIG. 2 is the amount of make-up fossil methane that is added to fuel the SMR unit 12 via the stream 26. Comparing Tables 1 and 2, the amount of fossil methane used in the comparative process is 152 MMBTU/hr, while the amount used in the inventive process that includes gas fermentation is 298 MMBTU/hr. Thus, the inventive process of FIG. 2 requires 146 MMBTU/hr of additional fossil methane. However, the process of FIG. 2 produces ethanol as a value added product (stream 28). The amount of ethanol produced in ethanol stream 28 is 110 MMBTU/hr. The production of ethanol in ethanol stream 28 more than off-sets the cost of additional methane in stream 26.

The amount of additional methane used, the amount of ethanol generated by the process of FIG. 2, as well as the increase in revenue from the hydrogen plant by the production of ethanol, despite additional methane use, is summarized in Table 3 below. In this example the addition of the fermentation step increases hydrogen plant revenue by 30.9%.

TABLE 3

Improved economics due to fermentation of purge gas

| ROW | Description | Stream/Basis | MMBTU/hr | $/MMBTU | $/hr | $/hr, percent of row A |
|---|---|---|---|---|---|---|
| A | Hydrogen revenue FIG. 1 | 22 | 1168 | $6.00 | $7,008 | 100.0% |
| B | FIG. 1 fossil methane make-up | 26 | 152 | $4.00 | $608 | 8.7% |
| C | FIG. 2 fossil methane make-up | 26 | 298 | $4.00 | $1,192 | 17% |
| D | Additional fossil methane cost FIG. 2 vs FIG. 1 | C-B | 146 | $4.00 | $584 | 8.3% |
| E | Ethanol revenues | 28 | 110 | $25.00 | $2,750 | 39.2% |
| F | Net benefit from fermentation FIG. 2 | E-D | N/A | N/A | $2,166 | 30.9% |

As shown in Table 3 above, revenue from producing the primary hydrogen product from hydrogen enriched stream 22 after recovery by PSA is $7,008/hr. Implementing the fermentation requires an additional cost of $584/hr due to the additional methane use in make-up (additional fossil methane cost of stream 26 in FIG. 2). However, the additional revenue from fermenting the hydrogen in the purge stream 24 to ethanol is $2,750/hr, which more than off-sets the $584/hr due to additional methane use in the make-up stream. The net benefit from implementing the fermentation of FIG. 2 is $2,166/hr, which represents a 30.9% increase in revenue relative to hydrogen production alone.

Advantageously, this increase in revenue is achieved without having an impact on heat integration, and uniquely benefits from the fermentation at the point in the hydrogen production process where the integration is possible and practical. Thus, a valuable fermentation product is produced from waste hydrogen in a purge gas stream that would otherwise be burned (e.g., for process energy). This increases product output from the hydrogen plant, with the added benefit of enabling efficient heat integration.

It should be appreciated that the foregoing examples are for illustrative purposes only and should not be construed to limit the current invention in any manner.

The invention claimed is:

1. An integrated hydrogen production process comprising:
   (i) providing a purge gas stream obtained from a process comprising the steps of:
      (a) converting fossil methane to carbon monoxide and hydrogen by reforming in a reforming unit;
      (b) converting at least a portion of the carbon monoxide by a water-gas shift reaction to carbon dioxide, thereby producing a stream comprising carbon dioxide and hydrogen; and (c) separating at least a portion of the hydrogen from the stream of step (b) from non-hydrogen components to produce a stream enriched in hydrogen and a purge gas stream comprising hydrogen and at least one of carbon dioxide, methane and carbon monoxide;

(ii) fermenting the purge gas stream, or a portion thereof, with microorganisms in one or more bioreactors to produce a fermentation product;

(iii) providing a fermentation exhaust gas stream from the one or more bioreactors, said exhaust gas stream comprising one or more combustible gases;

(iv) generating heat from the exhaust gas stream and using the heat to provide energy for the reforming unit;

(v) generating additional heat from a fuel gas stream and using the heat produced from the fuel gas stream to provide energy for the reforming unit, wherein the rate of fuel gas used to provide such additional heat is at least the rate of production of product energy associated with the fermentation product produced in step (ii), and wherein the rate of production is the heat of combustion of the fermentation product produced times the quantity of fermentation product produced measured in BTU/hr; and (vi) wherein the fermentation product is recovered.

2. The process of claim 1, wherein the step of separating comprises pressure swing adsorption.

3. The process of claim 1, wherein the fermentation product is butanol, ethanol, acetic acid or acetate.

4. The process of claim 3, wherein the fermentation product is ethanol.

5. The process of claim 1, wherein the hydrogen to carbon dioxide molar ratio of the purge gas stream is in the range of 2.5:1 to 3.5:1.5 (mol:mol).

6. The process of claim 1, further comprising generating heat from a portion of the purge gas stream and using the heat thus generated to provide energy for the reforming unit.

7. The process of claim 1, wherein the fermentation exhaust stream comprises at least carbon dioxide.

8. The process of claim 1, wherein the fuel gas stream comprises methane.

9. The process of claim 1, wherein the fuel gas stream is combined with the exhaust gas stream.

10. The process of claim 1, wherein the fermentation is carried out with a bacterial species from the genus *Clostridium*.

11. The process of claim 10, wherein the bacterial species is *Clostridium ljungdahlii*.

12. The process of claim 1, wherein the fermentation product produced in step (ii) is an alcohol.

13. The process of claim 12, further comprising providing the hydrogen produced in step (i)(c) to a hydroprocessing unit in an oil refinery and using the alcohol produced in step (ii) as a constituent in a refined product either directly or after subsequent processing.

14. The process of claim 13, wherein the alcohol is ethanol and the ethanol is subjected to subsequent processing comprising converting the ethanol to a hydrocarbon using a zeolite catalyst.

15. The process of claim 13, wherein the refined product is gasoline, diesel or jet fuel.

16. The process of claim 13, wherein the alcohol is ethanol.

17. The process of claim 13, wherein the alcohol is butanol.

18. The process of claim 1, wherein the reforming unit is a steam methane reforming unit or an autothermal reforming unit.

19. The process of claim 18, wherein the reforming unit is a steam methane reforming unit.

20. The process of claim 1, wherein the one or more combustible gases comprise hydrogen, methane or a combination thereof.

* * * * *

UNITED STATES PATENT AND TRADEMARK OFFICE
CERTIFICATE OF CORRECTION

| | | |
|---|---|---|
| PATENT NO. | : 9,145,300 B1 | Page 1 of 1 |
| APPLICATION NO. | : 14/600241 | |
| DATED | : September 29, 2015 | |
| INVENTOR(S) | : Patrick J. Foody | |

It is certified that error appears in the above-identified patent and that said Letters Patent is hereby corrected as shown below:

Title Page

In column 2 (page 1, item 56) at line 9, Under Other Publications, change ""Evoluotion" to --"Evolution--.

In column 2 (page 1, item 56) at line 9, Under Other Publications, change "Butonol-Gosoline" to --Butanol-Gasoline--.

In column 2 (page 1, item 56) at line 9, Under Other Publications, change "o Port" to --a Port--.

In column 2 (page 1, item 56) at line 10, Under Other Publications, change "Fuel-iniection, Spork-Ignition" to --Fuel-injection, Spark-Ignition--.

In the Specification

In column 5 at line 1, Change "authothermal" to --autothermal--.

In column 5 at line 13, Change "authothermal" to --autothermal--.

In column 9 at line 4, Change "naptha," to --naphtha,--.

In column 10 at line 37, Change "that that" to --that--.

Signed and Sealed this
Twenty-sixth Day of April, 2016

Michelle K. Lee
*Director of the United States Patent and Trademark Office*